United States Patent
Mueller et al.

(10) Patent No.: US 6,437,202 B2
(45) Date of Patent: Aug. 20, 2002

(54) FLUOROALKENE-NUCLEOPHILE ADDUCTS FOR ANALYSIS AND REMOVAL OF FLUOROALKENES

(75) Inventors: Mark Eugene Mueller, Marine on St. Criox; Donald Frederick Hagen, Woodbury; Yuri Cheburkov, Woodbury; Fred Lynn DeRoos, Woodbury; Glenn Delmont Johnson, Mahtomedi; John Stephen Marhevka, Maplewood; Venkateswarlu Pothapragada, Minneapolis, all of MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/880,279

(22) Filed: Jun. 13, 2001

Related U.S. Application Data

(62) Division of application No. 09/711,803, filed on Nov. 13, 2000, which is a continuation of application No. 09/154,350, filed on Sep. 16, 1988, now Pat. No. 6,147,268.

(51) Int. Cl.$^7$ ........................ C07C 17/38; B01D 39/00; B01D 24/00
(52) U.S. Cl. ........................... 570/179; 570/177
(58) Field of Search ................. 570/179, 177; 210/502.1, 503, 504

(56) References Cited

U.S. PATENT DOCUMENTS

| | | |
|---|---|---|
| 3,696,156 A | 10/1972 | Weeks |
| 4,437,271 A | 3/1984 | McAvoy |
| 5,233,107 A | 8/1993 | Jansen |
| 5,300,714 A | 4/1994 | Pothapragada et al. |
| 5,358,657 A * | 10/1994 | Sawyer et al. ......... 252/183.13 |
| 5,462,908 A | 10/1995 | Liang et al. |
| 5,507,941 A | 4/1996 | Pothapragada et al. |
| 5,529,686 A | 6/1996 | Hagen et al. |
| 5,635,060 A | 6/1997 | Hagen et al. |
| 5,895,826 A * | 4/1999 | Visca et al. .................. 570/179 |

FOREIGN PATENT DOCUMENTS

| | | |
|---|---|---|
| DD | 160 718 | 2/1984 |
| EP | 0 629 437 A | 12/1994 |
| EP | 0 828 258 A | 3/1998 |

OTHER PUBLICATIONS

Turbini, L. J., Zado, F. M., "Chemical and Environmental Aspects of Condensation Reflow Soldering", *Electronic Packaging and Production*, Jan. 1980, 49–59.
"Fluorinert Liquids", 3M Publication No. 98–0211–4411–2(78.2)R1 XY, Jun. 1988.
U.S. Defensive Publication T983,009 (Jun., 1979).
Hall et al. *Chemistry and Industry*, Mar. 6, 1989, p. 145–146.
England et al., *J. Fluorine Chem.* 1981, 17, 265–288.
Coffman et al., *J. Org. Chem.*, 1949, 14, 747–753.
"The Chemistry of Perfluoroisobutene," by Y.V. Zeifman et al., *Russian Chemical Reviews*, 1984, 53 (Mar.), 256–273.

* cited by examiner

*Primary Examiner*—Jafar Parsa
(74) *Attorney, Agent, or Firm*—Philip Y. Dahl

(57) ABSTRACT

A method for removing one or more fluorinated alkenes from a fluid comprises the step of contacting the fluid with an N-, S-, or P-containing nucleophile for a time sufficient to form an N-, S-, or P-containing nucleophile-fluoroalkene adduct. The nucleophile, and therefore the adduct, can be covalently bonded, coated or sorbed to a particulate support which can be enmeshed in a porous, fibrous web. In a preferred embodiment the fluorinated alkene can have the formula

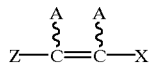

wherein A=F or $R_f$; X=H, F, Cl, $R_f$, or $YR_f$; Z=H, F, Cl, or $R_f$; and Y=O, N, or S; with the proviso that at least one A=F, and at most one of Z and X is H; wherein each $R_f$ is independently selected from the group consisting of highly fluorinated or perfluorinated alkyl groups; and a combination of any two $R_f$ groups can be linked to form a cyclic structure.

The $R_f$ alkyl chains may contain from 1-20 carbon atoms, with 1-12 carbon atoms preferred. The $R_f$ alkyl chains may be straight, branched, or cyclic. Preferably, $R_f$ is $CF_3$, $C_2F_5$, or $C_3F_7$.

11 Claims, No Drawings

FLUOROALKENE-NUCLEOPHILE ADDUCTS FOR ANALYSIS AND REMOVAL OF FLUOROALKENES

CROSS REFERENCE TO RELATED APPLICATIONS

This application is a divisional of U.S. application Ser. No. 09/711,803 filed Nov. 13, 2000, now pending, which is a continuation of U.S. application Ser. No. 09/154,350, filed Sep. 16, 1988, issued as U.S. Pat. No. 6,147,268.

FIELD OF THE INVENTION

This invention relates to fluoroalkene-nucleophile adduct formation for removal, immobilization, or quantification of fluoroalkenes from fluids.

BACKGROUND OF THE INVENTION

Perfluoroalkane fluids have many industrial uses, such as coolants for electronic devices (e.g., supercomputers) and as heat transfer media in vapor-phase soldering processes. However, upon transient heating many of these perfluorinated liquids at high temperatures, toxic impurities may form, such as certain fluoroalkenes, for example perfluoroisobutene (PFIB). These impurities may be hazardous to persons handling the liquid or operating equipment containing the contaminated liquid. Analytical procedures for the identification and quantification of the highly volatile low molecular weight fluorocarbons generally require chromatographic separation and reference standards for calibration. The more toxic perfluoroolefins such as PFIB are not readily available to be used as reference standards and transportation is a serious problem. Marhevka et al., *Anal. Chem.*, 1982, 54, 2607–2610, describe a method to generate a reference standard and suggest the use of an analytical surrogate, perfluorocyclopentene (PFCP), for calibration purposes.

Various methods have been suggested for reducing the hazard of PFIB exposure of operators of equipment that might inadvertently produce PFIB (Turbini, L. J., Zado, F. M., "Chemical and Environmental Aspects of Condensation Reflow Soldering", *Electronic Packaging and Production*, January, 1980, 49–59 and "Fluorinert Liquids", 3M Publication No. 98-0211-4411-2(78.2)R1 XY, June 1988). Some of these methods include techniques of operating and maintaining vapor-phase soldering equipment to avoid localized super-heating of perfluorinated liquids, thus reducing the amount of PFIB produced, and standards of designing work areas to provide sufficient ventilation to maintain PFIB levels at less than hazardous levels.

U.S. Defensive Publication T983,009 (June, 1979) describes a method of converting PFIB in a mixture of fluorine-containing compounds into a relatively nontoxic ether by contacting the mixture with a solution of methanol and a selected hydrogen halide. While this method does produce products which are generally less toxic than PFIB, it has disadvantages, including 1) being complex to perform in a continuous mode, since various feed streams of reactants must be controlled, 2) using hazardous hydrogen halides (e.g., HF and HCl) as reactants, and 3) yielding products which may create a disposal problem.

U.S. Pat. No. 3,696,156 describes a method of removing perfluoroolefin and perfluorochloroolefin impurities from saturated fluoroperhalocarbon compounds having two to six carbon atoms, by contacting the impure fluoroperhalocarbon in the vapor phase at about 180 to 250 degrees C with alumina containing a basic alkali metal or alkaline earth metal hydroxide or oxide.

U.S. Pat. No. 5,233,107 describes a process for removing olefinic impurities from hydrogen-containing chlorofluorocarbons in the gas phase at 200 to 400 degrees C over a zeolite. The contaminated higher boiling chlorofluorocarbons are preheated to convert the liquid to the gas phase in advance. The addition of 0.5 to 10% air or oxygen by volume to the process stream is recommended to keep coking at a very low level.

One of the disadvantages of processes utilizing elevated temperatures is that they require handling hot gases contaminated with hazardous compounds. In addition, certain fluorocarbons are unstable and generate a variety of olefinic and aliphatic impurities at elevated temperatures especially in the presence of catalytic surfaces.

Hall et al. *Chemistry and Industry*, March 6, 1989, 145-146, describe activated carbon filters to provide protection against exposure to PFIB and note that some of the PFIB is hydrolysed to produce 2H-perfluoroisobutyric acid and hydrogen fluoride. After storage and reuse of the exposed filter, 1,1,3,3,3-pentafluoropropene and 1,1,1,3,3,3-hexafluoropropane were found in the effluent stream.

A system and method for purifying saturated fluoroperhalocarbon liquids by removing olefinic impurities, such as PFIB, therefrom have been disclosed in U.S. Pat. Nos. 5,300,714 and 5,507,941. Inorganic oxide, hydroxide, carbonate, or phosphate particles are used in the method.

England et al., *J. Fluorine Chem.* 1981, 17, 265-288, describe reactions of amines with a dimer of hexafluoropropene and a perfluorovinyl sulfide prepared from hexafluoropropene. Anhydrous ammonia was added to a solution of hexafluoropropene dimer to form (1-amino-2,2,3,3,3-pentafluoropropylidene)propanedinitrile.

Coffman et al., *J. Org. Chem.*, 1949, 14, 747-753, reported that ammonia reacted with tetrafluoroethylene forms an amine which splits out HF to form difluoroacetonitrile which then forms a trimer.

An organic amine-impregnated activated carbon composition, which preferably has been pre-treated, has been used in breathing gas filters to enhance removal of various toxic perfluorocarbons as is disclosed in U.S. Pat. No. 5,462,908. There is no disclosure as to the composition of the treated material or the nature of the nucleophile used to form a stable immobilized adduct with fluoroalkenes.

An exhaustive review of one of the fluoroalkenes is presented in "The Chemistry of Perfluoroisobutene," by Y. V. Zeifman, et al., *Russian Chemical Reviews*, 1984, 53 (March), 256–273. Reactions of PFIB with numerous N, O, S, and P nucleophiles are discussed, without reference to their quantitative analytical application or the ability of these nucleophiles to react with other fluoroalkenes.

SUMMARY OF THE INVENTION

Briefly, this invention provides a method for removing one or more highly fluorinated or perfluorinated alkenes (also referred to hereinbelow as a "fluoroalkene") from a fluid, comprising the step of contacting the fluid with ammonium hydroxide or an organic nitrogen-, sulfur-, or phosphorus-containing nucleophile wherein the nucleophilic atom is N, S, or P (hereinafter sometimes referred to as N-, S-, or P-nucleophiles) for a time sufficient to form a nitrogen-, sulfur-, or phosphorus-containing nucleophile-fluoroalkene adduct. Preferably, the N-, S-, or P-nucleophile is sorbed on, or coated on, or bonded to, or itself can be, a support and can be used in a bed or cartridge. More preferably, the N-, S-, or P-nucleophile which can be sorbed on, or coated on, or bonded to a support is enmeshed in or forms a fibrous matrix, preferably a nonwoven matrix, which provides an essentially homogeneous, porous material. Alternatively the N-, S-, or P-nucleophile can be sorbed on, coated onto, or bonded directly to a porous matrix. Preferably, the nucleophile is ammonia or it comprises a nitrogen, sulfur or phosphorus nucleophile compound.

The optimum amount of nucleophile that can be loaded on a support varies with the nature of the support. In general, it is preferred to load the nucleophile in an amount in the range of 0.1 to 10 weight percent, more preferably 0.1 to 5 weight percent, based on the weight of the support.

In another aspect, the present invention provides a method for quantifying a highly fluorinated or perfluorinated alkene, for example PFIB, comprising the steps of a) providing a stable or unstable N-, S-, or P-containing nucleophile-fluoroalkene adduct, which may be sorbed to a support, and b) quantifying for highly fluorinated or perfluorinated alkenes in a fluid by either 1) measuring highly fluorinated or perfluorinated alkenes when the N-, S-, or P-containing nucleophile-fluoroalkene adduct is stable, displacing the adduct from the support when necessary, or 2) measuring the fluoride ion for indirect quantification of highly fluorinated or perfluorinated alkenes, when the N-, S-, or P-containing nucleophile-fluoroalkene is unstable and produces fluoride ion.

In yet another aspect, the present invention describes a method for preparing an adduct comprising the step of contacting an immobilized N-, S-, or P-containing nucleophile with a fluid comprising a fluoroalkene for a time sufficient to form an N-, S-, or P-containing nucleophile-fluoroalkene adduct.

In still another aspect, the present invention provides a reactive particulate comprising an N-, S-, or P-containing nucleophile bonded or sorbed to a support which preferably has a high surface area. The reactive particulate can react with a highly fluorinated or perfluorinated alkene to produce an N-, S-, or P-containing nucleophile-fluoroalkene adduct.

In a further aspect, the present invention provides N-, S-, or P- containing nucleophile-fluoroalkene adducts which have eliminated HF to form new nucleophile-substituted olefinic compounds and which can be made to further react with other nucleophiles such as water or an alcohol to form a new secondary adduct which undergoes further reactions to form an amide or a vinyl ether when a nitrogen nucleophile was used to prepare the initial nucleophile-fluoroalkene adduct.

In a still further aspect, there are provided stable fluoroalkene-nucleophile derivatives which can be used as analytical standards for quantification and identification of the more toxic fluoroalkene species, reducing the difficulties of manufacture and shipping hazardous material.

As used in this application:

"Adduct" means the addition product of a nucleophile and a fluoroalkene with or without the elimination of a byproduct;

"fluid" refers to a material that is either a liquid or a gas at 25° C. and 760 mm Hg pressure, i.e., standard conditions;

"fluoroalkene" and "fluoroolefin" are used interchangeably;

"highly fluorinated alkene" means that more than half of the hydrogen atoms on the alkene have been replaced with fluorine atoms. It is preferred that the carbon atoms immediately adjacent to the unsaturated carbon-carbon bond of "highly fluorinated alkenes" will have more than half the total number of hydrogen atoms directly bonded to them replaced with fluorine atoms, and most preferably the highly fluorinated alkene is a perfluorinated alkene;

"highly fluorinated alkyl group" will have more than half the total number of hydrogen atoms replaced with fluorine atoms. Although hydrogen atoms may remain, it is preferred that all hydrogen atoms be replaced with fluorine to form a perfluoroalkyl group;

"stable" means that the fluoroalkene-nucleophile adduct can survive the thermal stress it is subjected to when injected into a gas chromatographic column at elevated temperatures needed to elute, identify, and quantify the compounds of interest; and "nitrogen-, sulfur-, or phosphorus-nucleophile" ("N-, S-, or P-nucleophile") means any nucleophile comprising one or more of nitrogen, sulfur, or phosphorus as the nucleophilic site, and includes ammonia and any organic nucleophiles comprising one or more of nitrogen, sulfur, or phosphorus as the nucleophilic site.

A fluoroalkene of particular interest for quantifying in or removal from fluids is PFIB, which, because of its very toxic nature, is not available commercially for analytical instrument calibration. 2-Perfluorobutene, which is readily available (Lancaster Chemicals Inc., Lancaster, Pa.), can be chosen as a surrogate of close structure analogous to PFIB for calibration purposes in the present invention.

In a still further aspect, there is provided a porous, preferably non-woven, fibrous matrix, preferably a sheet material, comprising an immobilized reactive or sorptive N-, S-, or P-containing nucleophile coated on high surface area particulate entrapped in the fibrous sheet material, that upon reaction with a fluoroalkene produces a nucleophile-fluoroalkene adduct. The high surface area and close proximity of the entrapped sorptive particles results in rapid reaction kinetics due to the minimal diffusion distances between particles. Porous non-woven fibrous matrices useful in the present invention for immobilizing nucleophile-coated particles are disclosed, for example, in U.S. Pat. No. 5,635,060, which is incorporated herein by reference.

The present invention provides advantages in removing and quantifying the levels of fluoroalkenes in fluids. The quantitative method of the present invention permits positive identification of individual highly fluorinated or perfluorinated alkenes with a thousand-fold increase in sensitivity of quantitative measurements compared with existing gas chromatographic methods. In order to avoid contamination of fluids having high vapor pressure by generation of a toxic volatile highly fluorinated or perfluorinated alkene therein, the present invention provides a relatively nonvolatile adduct for removing such potential contaminants.

The present invention method is also advantageous in that stability of the adduct can be selected. In some embodiments, it may be desirable to produce an unstable adduct so as to decompose or remove highly fluorinated or perfluorinated alkenes. Hydrous ammonia (ammonium hydroxide), for example, forms an unstable series of adducts which release HF and appears to completely de-fluorinate PFIB to form tricyanomethane with the release of 8 fluoride ions. This is in contrast to England et al., supra, where anhydrous ammonia, when reacted with hexafluoropropylene dimer, formed a dicyanofluorocarbon, (1-amino-2,2,3,3-pentafluoropropylidene)propanedinitrile.

A sorbent can be used to sorb the reaction products. For example, molecular sieves such as Silicalite™, a hydrophobic zeolite (UOP, Tarrytown, N.Y.), can be useful to sorb hydrogen fluoride (HF) and trap other low molecular weight reaction products, both of which can be produced when highly fluorinated or perfluorinated alkenes react with certain nucleophiles. In the present invention, Silicalite can act as a substrate for immobilizing the nucleophiles of the present invention and as a reactant and sorbent for reaction products. It is a preferred substrate in that it is not deactivated by water because of its six Angstrom pore size which prevents water molecule clusters from entering the high surface area interior of the particle.

In the present invention heating is not required to activate the nucleophiles. The present invention method takes place at room temperature (20-25 degrees C) and no pre-treatment of the nucleophile, as in U.S. Pat. No. 5,462,908, is required.

DETAILED DESCRIPTION OF PREFERRED EMBODIMENTS OF THE INVENTION

Highly fluorinated or perfluorinated alkenes that can be removed, immobilized, or quantified according to the method of the invention include alkenes of the formula

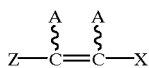

wherein A=F or $R_f$; X=H, F, Cl, $R_f$, or $YR_f$; Z=H, F, Cl, or $R_f$; and Y=O, N, or S; with the proviso that at least one A=F, and at most one of Z and X is H; wherein each $R_f$ is independently selected from the group consisting of highly fluorinated or perfluorinated alkyl groups; and a combination of any two $R_f$ groups can be linked to form a cyclic structure.

The $R_f$ alkyl chains may contain from 1-20 carbon atoms, with 1-12 carbon atoms preferred. The $R_f$ alkyl chains may be straight, branched, or cyclic. Up to twenty heteroatoms or radicals such as divalent oxygen, trivalent nitrogen or hexavalent sulfur may interrupt the skeletal chain, as is well recognized in the art. When $R_f$ is or contains a cyclic structure, such structure preferably has 5 or 6 ring members, 1 or 2 of which can be heteroatoms. "Highly fluorinated" means that the degree of fluorination on the chain is sufficient to provide the chain with properties, particularly electronic properties, similar to those of a perfluorinated chain. More particularly, a highly fluorinated alkyl group will have more than half the total number of hydrogen atoms replaced with fluorine atoms. Although hydrogen atoms may remain, it is preferred that at least two hydrogens on each carbon attached to the vinylic carbon atoms be replaced by fluorine, and it is more preferred that all hydrogen atoms be replaced with fluorine to form a perfluoroalkyl group. It is more preferred that at least two out of three hydrogens on the alkyl group be replaced with fluorine, still more preferred that at least three of four hydrogen atoms be replaced with fluorine and most preferred that all hydrogen atoms be replaced with fluorine to form a perfluorinated alkyl group. Preferably, $R_f$ is $CF_3$, $C_2F_5$ or $C_3F_7$.

The ability of highly fluorinated and perfluorinated alkenes to react with nuclcophiles is known (see, for example, Zeifman, supra), and is believed to be caused by the high electrophilicity of the carbon-carbon double bond, which, in turn, is believed to be due to the strong electron withdrawing effects of fluorine atoms and $R_f$ groups, particularly $CF_3$ groups, attached thereto, as well as the capacity of vinylic fluorine atoms to effectively conjugate with the carbon-carbon double bond. Of the known fluoroalkenes, perfluoroisobutene (PFIB), having the chemical formula

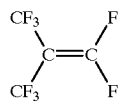

can be regarded as the most reactive towards nucleophiles, which Zeifman (supra) attributed to the highly electrophilic character of the carbon-carbon double bond, the lability of the fluorine atoms of the $CF_3$ group, and the possibility of further reactions of any nucleophile addition products due to the high CH-acidity of, e.g., a $(CF_3)_2CH$—$CF_2$-group that may be formed by such an addition reaction.

Nucleophiles capable of reacting with highly fluorinated and perfluorinated alkenes include those comprising a nitrogen-, sulfur- or phosphorus nucleophilic site. Nitrogen-containing nucleophiles useful in the present invention include ammonia, primary amines, and secondary amines, preferably secondary amines. Ammonia is known to react with, for example, PFIB, to yield hexafluoroisobutyronitrile and hydrogen fluoride (Zeifman, supra).

Primary amines useful in the present invention include, in principle, all known primary amines, including aliphatic, aromatic, saturated and unsaturated heterocyclic primary amines. Although primary amines are not the preferred amine nucleophile of the present invention, liquid primary amines that can be easily and safely handled under ambient conditions (e.g. 25° C. and one atmosphere pressure), and that readily adsorb or absorb onto a substrate or carrier, as described below, can be suitable nucleophiles for the present invention. Non-limiting examples of such primary amines include propyl amine, n-butyl amine, ethylenediamine, n-octyl amine, aniline, cyclohexylamine, benzylamine, and a myriad of amines known in the art.

Secondary amines are preferred in the present invention, and, in principle, can include all known secondary amines, including aliphatic, aromatic, saturated and unsaturated heterocyclic secondary amines. Secondary amines are preferred in the present invention because they can be capable of a 1:1 molar reaction with a highly fluorinated or perfluorinated alkene whereby any further reaction of the amine-fluoroalkene adduct with the secondary amine is unlikely, such that cleaner, more homogeneous reaction products can be produced. Non-limiting examples of secondary amines useful in the invention include dimethylamine, diethylamine, dibutylamine, dibenzylamine, morpholine, N-methyl aniline, methylbenzylamine, piperidine, pyrrole, pyrrolidine, pyrrolidinone, and piperazine. Preferably, secondary amines useful in the present invention include heterocyclic compounds, non-limiting examples of which include morpholine, piperidine, pyrrole, and pyrrolidine. Heterocyclic secondary amines are preferred because of their ease of handling and their ready reactivity. Morpholine is the most preferred secondary amine, for purposes of the present invention.

As noted above, the lability of fluorine atoms in the reaction of amines with fluoroalkenes can generate hydrogen fluoride, HF. Therefore, the reaction can be driven to completion by effective removal of HF. For this reason, amines are the preferred nucleophile for the present invention, since essentially all known amines exhibit sufficient basicity to scavenge the HF as it is formed, so that the reaction is driven to completion. As described in more detail below, the generation and quantification of HF in these reactions provides a useful means of measuring the amount of fluoroalkene in a fluid.

Sulfur-containing nucleophiles useful in the invention comprise those that are capable of forming a sulfide anion upon reaction with a base. Examples include thiophenol, benzyl mercaptan, allyl mercaptan, and salts thereof, such as mercaptides and thiophenoxides. The reaction of fluoroalkenes with sulfur nucleophiles can produce either HF or MF, where M is a metal such as sodium, potassium, or the like, that forms the mercaptide or thiophenoxide salt, and disubstitution to replace both vinylic fluorine atoms can take place readily.

Phosphorus-containing nucleophiles useful in the invention can include trialkyl phosphites (e.g., trimethyl phosphite, triethyl phosphite, tri-n-propyl phosphite, tri-n-butyl phosphite), dialkyl phosphines (e.g., di-isopropyl phosphine), and trialkyl phosphines (e.g., trimethyl phosphine, triethyl phosphine, tri-n-propyl phosphine, tri-n-butyl phosphine).

Particulate supports to which nucleophiles of the invention can be bonded or upon which nucleophiles can be sorbed include those that are substantially insoluble in any aqueous or organic fluids comprising fluoroalkenes that are to be adsorbed, remediated, or quantified by methods of the invention. "Organic fluids" includes highly fluorinated or perfluorinated working fluids known in commerce, such as refrigerants, thermal management fluids, dielectric fluids, and the like. The particle can be an organic polymer, for example, poly(divinylbenzene), poly(styrene-co-divinylbenzene), or poly- or copoly-(meth)acrylic acid esters, and derivatives thereof; inorganic oxide particles, for example, silica, alumina, titania, zirconia and other ceramic materials, to which optionally organic groups can be bonded or coated, or which can be coated with aqueous- or organic-insoluble, non-swellable sorbent material or the surface (internal and/or external) of which can be derivatized to provide a coating of insoluble, non-swellable sorbent material; carbon particles, particularly activated charcoal; molecular sieves, polymer-coated, carbon-clad inorganic oxide particles, such as those described in U.S. Pat. No. 5,271,833, and the like.

Particulate materials useful in the invention can have a diameter of from about 0.1 to about 600 micrometers, preferably in the range of 1-100 micrometers, more preferably in the range of 3 to 100 micrometers. Particle size is chosen so as to maximize available surface area while also optimizing fluid flow rate through the particle matrix. Preferably the surface area is in the range of 50 to 1000 meter$^2$/gram or more. Particulate supports can have a regular shape, for example spherical, or an irregular shape. It has been found advantageous in some instances to use particulate materials in two or more particle size ranges falling within the broad range.

The insoluble, aqueous- or organic-insoluble, non-swellable sorbent coatings useful in the invention generally have a thickness in the range of one molecular layer to about 100 nanometers. Many particles having coated surfaces are known, including modified silica particle, for example, silica particle having bonded thereto organic groups, preferably cyanopropyl, cyclohexyl, phenyl, ethyl, butyl, octyl, and octadecyl groups. Such coatings preferably readily sorb nucleophiles of the invention and are inert toward them.

Sorptive coatings which can be applied to particulate materials can be either thin mechanical coatings of insoluble, non-swellable polymers such as crosslinked silicones, poly(butadienes), etc., or covalently bonded organic groups such as aliphatic groups of varying chain length (for example, from 2 to 18 carbon atoms).

Molecular sieves useful in the invention, which include zeolites, are inorganic, crystalline materials, usually aluminosilicate compositions, in which the crystal framework of aluminum and silicon atoms forms a three-dimensional network of internal cavities having a honeycomb-like structure. Many molecular sieves of varying size and constitution are commercially available.

A particularly useful molecular sieve is Silicalite inorganic hydrophobic zeolite commercially available from UOP, Tarrytown, N.Y., under the trade name Abscents™.

A coconut-based activated charcoal particulate for use in the invention is preferred.

The particles of the invention can be enmeshed in various porous, fibrous, nonwoven webs or matrices. Types of webs or matrices include fibrillated-polytetrafluoroethylene (PTFE), microfibrous webs, macrofibrous webs, and polymer pulps. Alternatively, in use, particles can be held in a bed, including a fluidized bed, or packed in a column or tube. Nucleophilic materials can be coated or sorbed onto particulate prior to or after the particulate becomes enmeshed in a web or is placed in a bed or packed in a column.

Many types of fibrous, nonwoven webs or matrices can be useful in the invention, including;

1. Fibrillated PTFE

PTFE composite sheet material can be prepared by blending the particulate or combination of particulates employed with an aqueous PTFE emulsion until a uniform dispersion is obtained and adding a volume of process lubricant up to approximately one half the volume of the blended particulate. Blending takes place along with sufficient process lubricant to exceed sorptive capacity of the particles in order to generate the desired porosity level of the resultant article. Preferred process lubricant amounts are in the range of 3 to 200 percent by weight in excess of that required to saturate the particulate, as is disclosed in U.S. Pat. No. 5,071,610. The aqueous PTFE dispersion is then blended with the particulate mixture to form a mass having a putty-like or dough-like consistency. The sorptive capacity of the solids of the mixture is noted to have been exceeded when small amounts of water can no longer be incorporated into the mass without separation. This condition should be maintained throughout the entire mixing operation. The putty-like mass is then subjected to intensive mixing at a temperature and for a time sufficient to cause initial fibrillation of the PTFE particles. Preferably, the temperature of intensive mixing is up to 90° C., preferably it is in the range of 0° to 90° C., more preferably 20° to 60° C.

Preferably, the weight ratio of particulate to PTFE is in the range of 40:1 to 1:40, more preferably 30:1 to 1:30, and most preferably in the range of 20:1 to 1:20.

Mixing times will typically vary from 0.2 to 2 minutes to obtain the necessary initial fibrillation of the PTFE particles. Initial mixing causes partial disoriented fibrillation of a substantial portion of the PTFE particles.

Initial fibrillation generally will be noted to be at an optimum within 60 seconds after the point when all components have been fully incorporated into a putty-like (dough-like) consistency.

Devices employed for obtaining the necessary intensive mixing are commercially available intensive mixing devices which are sometimes referred to as internal mixers, kneading mixers, double-blade batch mixers as well as intensive mixers and twin screw compounding mixers. The most popular mixer of this type is the sigma-blade or sigma-arm mixer. Some commercially available mixers of this type are those sold under the common designations Banbury mixer, Mogul mixer, C. W. Brabender Prep mixer and C. W. Brabender sigma blade mixer. Other suitable intensive mixing devices may also be used.

The soft putty-like mass is then transferred to a calendering device where the mass is calendered between gaps in calendering rolls preferably maintained at a temperature up to 125° C., preferably in the range of 0° to about 100° C., more preferably in the range of 20° C. to 60° C., to cause additional fibrillation of the PTFE particles of the mass, and consolidation while maintaining the water level of the mass at least at a level of near the sorptive capacity of the solids, until sufficient fibrillation occurs to produce the desired nonwoven web. Preferably the calendering rolls are made of a rigid material such as steel. A useful calendering device has a pair of rotatable opposed calendering rolls each of which may be heated and one of which may be adjusted toward the other to reduce the gap or nip between the two. Typically, the gap is adjusted to a setting of 10 millimeters for the initial pass of the mass and, as calendering operations progress, the gap is reduced until adequate consolidation occurs. At the end of the initial calendering operation, the resultant sheet is folded and then rotated 90° to obtain biaxial fibrillation of the PTFE particles. Smaller rotational angles (e.g., 20° to less than 90°) may be preferred in some extraction and chromatographic applications to reduce calender biasing, i.e., unidirectional fibrillation and orientation. Excessive calendering (generally more than two times) reduces the porosity which in turn reduces the flow-through rate.

During calendering, the lubricant level of the mass is maintained at least at a level of exceeding the absorptive capacity of the solids by at least 3 percent by weight, until sufficient fibrillation occurs and to produce porosity or void volume of at least 30 percent and preferably 40 to 70 percent of total volume. Increased lubricant results in increased pore size and increased total pore volume as is disclosed in U.S. Pat. No. 5,071,610.

The calendered sheet is then dried under conditions which promote rapid drying yet will not cause damage to the composite sheet or any constituent therein. Preferably drying is carried out at a temperature below 200° C. The preferred means of drying is by use of a forced air oven. The preferred drying temperature range is from 20° C. to about 70° C. The most convenient drying method involves suspending the composite sheet at room temperature for at least 24 hours. The time for drying may vary depending upon the particular composition, some particulate materials having a tendency to retain water more than others.

The resultant composite sheet preferably has a tensile strength when measured by a suitable tensile testing device such as an Instron (Canton, Mass.) tensile testing device of at least 0.5 MPa. The resulting composite sheet has uniform porosity and a void volume of at least 30 percent of total volume.

The PTFE aqueous dispersion employed in producing the PTFE composite sheet usefull in this invention is a milky-white aqueous suspension of minute PTFE particles. Typically, the PTFE aqueous dispersion will contain about 30 percent to about 70 percent by weight solids, the major portion of such solids being PTFE particles having a particle size in the range of about 0.05 to about 0.5 micrometers. The commercially available PTFE aqueous dispersion may contain other ingredients, for example, surfactant materials and stabilizers which promote continued suspension of the PTFE particles.

Such PTFE aqueous dispersions are presently commercially available from Dupont de Nemours Chemical Corp. (Wilmington, Del.), for example, under the trade names Teflon™ 30, Teflon™ 30B or Teflon™ 42. Teflon™ 30 and Teflon™ 30B contain about 60 percent solids by weight which are for the most part 0.05 to 0.5 micrometer PTFE particles and from about 5.5 percent to about 6.5 percent by weight (based on weight of PTFE resin) of non-ionic wetting agent, typically octylphenol polyoxyethylene or nonylphenol polyoxyethylene. Teflon 42 contains about 32 to 35 percent by weight solids and no wetting agent but has a surface layer of organic solvent to prevent evaporation. A preferred source of PTFE is FLUONM, available from ICI Americas, Inc. Wilmington, Del.

In other embodiments of the present invention, the fibrous membrane (web) can comprise non-woven, macro- or microfibers preferably selected from the group of fibers consisting of polyamide, polyolefin, polyester, polyurethane, glass fiber, polyvinylhalide, or a combination thereof. The fibers preferably are polymeric. (If a combination of polymers is used, a bicomponent fiber may be obtained.) If polyvinylhalide is used, it preferably comprises fluorine of at most 75 percent (by weight) and more preferably of at most 65 percent (by weight). Addition of a surfactant to such webs may be desirable to increase the wettability of the component fibers.

2. Macrofibers

The web can comprise thermoplastic, melt-extruded, large-diameter fibers which have been mechanically-calendered, air-laid, or spunbonded. These fibers have average diameters in the general range of 50 μm to 1,000 μm.

Such non-woven webs with large-diameter fibers can be prepared by a spunbond process which is well known in the art. (See, e.g., U.S. Pat. Nos. 3,338,992, 3,509,009, and 3,528,129.) As described in these references, a post-fiber spinning web-consolidation step (i.e., calendering) is required to produce a self-supporting web. Spunbonded webs are commercially available from, for example, AMOCO, Inc. (Napierville, Ill.).

Non-woven webs made from large-diameter staple fibers can also be formed on carding or air-laid machines (such as a Rando-Webber™ Model 12BS made by Curlator Corp., East Rochester, N.Y.), as is well known in the art. See, e.g., U.S. Pat. Nos. 4,437,271, 4,893,439, 5,030,496, and 5,082,720.

A binder is normally used to produce self-supporting webs prepared by the air-laying and carding processes and is optional where the spunbond process is used. Such binders can take the form of resin systems which are applied after web formation or of binder fibers which are incorporated into the web during the air laying process.

Examples of common binder fibers include adhesive-only type fibers such as Kodel™ 43UD (Eastman Chemical Products, Kingsport, Tenn.) and bicomponent fibers, which are available in either side-by-side form (e.g., Chisso ES Fibers, Chisso Corp., Osaka, Japan) or sheath-core form (e.g., Melty™ Fiber Type 4080, Unitika Ltd., Osaka, Japan). Application of heat and/or radiation to the web "cures" either type of binder system and consolidates the web.

Generally speaking, non-woven webs comprising macrofibers have relatively large voids. Therefore, such webs have low capture efficiency of small-diameter particulate (reactive supports) which is introduced into the web. Nevertheless, particulate can be incorporated into the non-woven webs by at least four means. First, where relatively large particulate is to be used, it can be added directly to the web, which is then calendered to actually enmesh the particulate in the web (much like the PTFE webs described previously). Second, particulate can be incorporated into the primary binder system (discussed above) which is applied to the non-woven web. Curing of this binder adhesively attaches the particulate to the web. Third, a secondary binder system can be introduced into the web. Once the particulate is added to the web, the secondary binder is cured (independent of the primary system) to adhesively incorporate the particulate into the web. Fourth, where a binder fiber has been introduced into the web during the air laying or carding process, such a fiber can be heated above its softening temperature. This adhesively captures particulate which is introduced into the web. Of these methods involving non-PTFE macrofibers, those using a binder system are generally the most effective in capturing particulate. Adhesive levels which will promote point contact adhesion are preferred.

Once the particles have been added, the loaded webs are typically further consolidated by, for example, a calendering process. This further enmeshes the particles within the web structure.

Webs comprising larger diameter fibers (i.e., fibers which average diameters between 50 $\mu$m and 1,000 $\mu$m) have relatively high flow rates because they have a relatively large mean void size.

3. Microfibers

When the fibrous web comprises non-woven microfibers, those microfibers provide thermoplastic, melt-blown polymeric materials having active particles dispersed therein. Preferred polymeric materials include such polyolefins as polypropylene and polyethylene, preferably further comprising a surfactant, as described in, for example, U.S. Pat. No. 4,933,229. Alternatively, surfactant can be applied to a blown microfibrous (BMF) web subsequent to web formation. Polyamide can also be used. Particulate can be incorporated into BMF webs as described in U.S. Pat. No. 3,971,373.

Microfibrous webs of the present invention have average fiber diameters up to 50 $\mu$m, preferably from 2 $\mu$m to 25 $\mu$m, and most preferably from 3 $\mu$m to 10 $\mu$m. Because the void sizes in such webs range from 0.1 $\mu$m to 10 $\mu$m, preferably from 0.5 $\mu$m to 5 $\mu$m, flow through these webs is not as great as is flow through the macrofibrous webs described above.

4. Cast Porous Membranes

Solution-cast porous membranes can be provided by methods known in the art. Such polymeric porous membranes can be, for example, polyolefin including polypropylene, polyamide, polyester, polyvinyl chloride, and polyvinyl acetate fibers.

5. Fibrous Pulps

The present invention also provides the use of a sheet material comprising a porous fibrous pulp, preferably a polymeric pulp, comprising a plurality of fibers that mechanically entrap active particles, and preferably the sheet also comprises a polymeric hydrocarbon binder, the weight ratio of particles to binder being at least 13:1 and the ratio of average uncalendered sheet thickness to effective average particle diameter being at least 125:1.

Generally, the fibers that make up the porous polymeric pulp of the sheet material useful in the present invention can be any pulpable fiber (i.e., any fiber that can be made into a porous pulp). Preferred fibers are those that are stable to radiation and/or to a wide range of pH (1 through 14). Examples include polyamide fibers and those polyolefin fibers that can be formed into a pulp including, but not limited to, polyethylene and polypropylene. Particularly preferred fibers are aromatic polyamide fibers and aramid fibers because of their stability to both radiation and highly caustic fluids. Examples of useful aromatic polyamide fibers are those fibers of the nylon family. Polyacrylic nitrile, cellulose, and glass can also be used. Combinations of pulps can be used.

Examples of useful aramid fibers are those fibers sold under the trade name Kevlar™ (DuPont, Wilmington, Del.). Kevlar fiber pulps are commercially available in three grades based on the length of the fibers that make up the pulp. Regardless of the type of fiber(s) chosen to make up the pulp, the relative amount of fiber in the resulting sheet (when dried) ranges from about 12.5 percent to about 30 percent (by weight), preferably from about 15 percent to 25 percent (by weight).

Useful binders for sheets useful in the present invention are those materials that are stable over a range of pH (especially high pH) and that exhibit little or no interaction (i.e., chemical reaction) with any of the fibers of the pulp, the particles entrapped therein, or fluoroalkenes. Polymeric hydrocarbon materials, originally in the form of latexes, have been found to be especially useful. Common examples of useful binders include, but are not limited to, natural rubbers, neoprene, styrene-butadiene copolymer, acrylate resins, and polyvinyl acetate. Preferred binders include neoprene and styrene-butadiene copolymer. Regardless of the type of binder used, the relative amount of binder in the resulting sheet (when dried) is about 3 percent to about 7 percent, preferably about 5 percent. The preferred amount has been found to provide sheets with nearly the same physical integrity a sheets that include about 7 percent binder while allowing for as great a particle loading as possible. It may be desirable to add a surfactant to the fibrous pulp, preferably in small amounts up to about 0.25 weight percent of the composite.

Because the capacity and efficiency of the sheet depends on the amount of particles included therein, high particle loading is desirable. The relative amount of particles in a given sheet material useful in the present invention is preferably at least about 65 percent (by weight), more preferably at least about 70 percent (by weight), and most preferably at least about 75 percent (by weight). Additionally, the weight percentage of particles in the resulting sheet is at least 13 times greater than the weight percentage of binder, preferably at least 14 times greater than the weight percentage of binder, more preferably at least 15 times greater than the weight percentage of binder.

Regardless of the type or amount of the particles used in the sheet material useful in the present invention, they are mechanically entrapped or entangled in the fibers of the porous pulp. In other words, the particles are not covalently bonded to the fibers.

The method of reacting a nucleophile, particularly an amine or a nitrogen-containing nucleophile, with a fluoroalkene as described herein finds utility in absorbing and removing the fluoroalkenes from fluids in which they may be present. In the invention, "removal" includes chemical reactions that destroy or sufficiently change or reduce the volatility or toxicity of fluoroalkenes. Such chemical reactions may liberate hydrogen fluoride (HF), such that determination of the amount of HF liberated provides an indirect measure of the amount of fluoroalkene in the fluid. Thus, the method of the invention is useful for remediation of highly fluorinated or perfluorinated working fluids, including industrial reaction and waste streams, to remove potentially toxic or dangerous fluoroalkenes, the most notable of which is PFIB. In addition, the method of the invention provides a convenient, direct method for quantification of certain fluoroalkenes due to precise identification of fluoroalkene-nucleophile adduct(s) by, for example, GC/MS methods. Finally, the method of the invention provides a means of continuous cleaning of highly fluorinated and perfluorinated working fluids by circulating them through a bed or column or particle-loaded fibrous web comprising support particles to which or on which nucleophiles are sorbed or coated.

In a preferred embodiment of the invention, an amine, preferably a secondary amine, and more preferably morpholine, was adsorbed onto silica gel particles that previously had been packed into a tube. A fixed amount of fluid containing a fluoroalkene was passed through the tube, and the effluent was analyzed by GC/MS for the presence of the fluoroalkene to determine the capacity of the tube.

Alternatively, particles, such as activated charcoal, can be enmeshed in a fibrillated PTFE web, such as are commercially available as Empore™ nonwoven webs, from 3M, St. Paul, Minn. Preferably, the activated charcoal particles are coated with morpholine by soaking the particle-loaded Empore™ web in morpholine solution, then air-drying the web to remove residual solvent. Then the fluid containing a fluoroalkene to be quantified or removed is passed through the morpholine treated web which is placed in a standard solid phase extraction (SPE) web holder.

Objects and advantages of this invention are further illustrated by the following examples, but the particular materials and amounts thereof recited in these examples, as well as other conditions and details, should not be construed to unduly limit this invention.

Perfluorinated liquids can be used as coolants for electronic devices (e.g., supercomputers) and as heat transfer media in vapor-phase soldering processes. Toxic fluoroalkene impurities can form upon transient heating of perfluorinated liquids which are used in many industrial processes. The methods and materials of the present invention are environmentally advantageous because (1) they can be used to remove fluoroalkenes, including PFIB, from fluids frequently used in industry and (2) they teach methods to detect and monitor the presence of these reactive fluoroalkenes at low levels.

EXAMPLES

All materials not otherwise identified in the examples were purchased from Aldrich Chemical Co., Milwaukee, Wis.

Example 1

Reactions of PFIB with Ammonium Hydroxide to Form Unstable Adducts

A gas standard containing 10 µL PFIB (Fluorochem, Ltd. Derbyshire, UK) per mL of air was prepared in a glass sampling bulb. One hundred µL of this gas standard was mixed with 40 mL of perfluorohexane ($FC_{72}$, commercially available from 3M Inert Fluids Group, St. Paul, Minn.) to give a nominal concentration of 25 nL gaseous PFIB per mL solution. Eight mL aliquots of this standard solution were vortexed (shaken vigorously) for seven minutes in 14 mL volume polystyrene centrifuge tubes (Falcon™ brand, #2001, VWR Scientific Products, South Plainfield, N.J.) together with 0.2 mL of concentrated (34 wt %) ammonium hydroxide. After this, each sample was treated with 2 mL of a special total ionic strength adjusting buffer (TISAB-B, nominal 4 molar acetic acid/potassium acetate buffer at pH=5.0, described in Orion Fluoride ion selective electrode (ISE) manuals, Orion Corp. Beverly, Mass.). The samples were vortexed again, after which phase separation took place. An Orion combination Fluoride ISE in combination with an Orion 920 ISE meter was used to measure fluoride concentration of the aqueous phase in the sample tube. Control samples of perfluorohexane without PFIB were carried through the entire process, as was a TISAB-B/ammonia blank, neither of which reacted. PFIB in the solution of perfluorohexane when mixed with hydrous ammonia (ammonium hydroxide) formed an unstable addition product, which spontaneously eliminated HF forming a second fluoroalkene species. This was followed by sequential addition reactions of ammonia with the alkenes produced by the elimination of HF, to form secondary adducts and subsequent elimination reactions of HF from the adducts until the starting PFIB was highly defluorinated. Fluoride ion concentration observed was proportional to PFIB added to the solutions, and recovery of fluoride ion from PFIB was eighty percent of theoretical total fluorine. These proposed reactions are shown in Reaction Sequence 1 below.

As a comparative, 1H-pentadecafluoroheptane (a representative hydrofluoroalkane) was evaluated in the liquid solution mode for reactivity with ammonia/ammonium hydroxide. There was no measurable reaction at room temperature when vortexed for ten minutes in the same manner as described for the PFIB liquid solution samples under the conditions previously described.

The data from this Example show that these reaction conditions removed nearly all the S fluorine from PFIB but did not dehydrofluorinate hydrofluoroalkanes containing $CF_2H$-group to form fluoride ions.

Reaction Scheme 1
Unstable Ammonia-PFTB Adducts

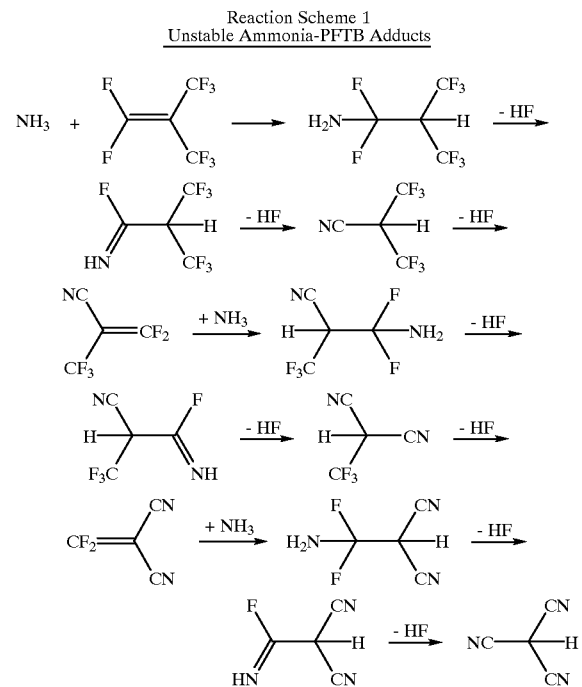

Example 2

PFIB Adduct Formation with Ammonium Hydroxide on Solid Supports

A vapor phase assay was developed using ammonium hydroxide sorbed on solid supports packed in glass sampling tubes. The tube types were: 1) Acid-mist silica tubes (cat. #226-10-03), 2) Silica tubes (cat. #226-15), and 3) Charcoal tubes (cat. #226-09), all from SKC Inc., Fullerton, Calif. The tubes were evaluated both as received (untreated) and by loading each of them with 200 µL of concentrated ammonium hydroxide (treated) and subsequently sealing them with plastic caps until they were evaluated.

A gas standard containing 10 nL PFIB (Fluorochem, cited above) per mL of air (10 ppm PFIB) was prepared in a glass sampling bulb. Portions of this standard accurately diluted in air or in nitrogen were passed through these tubes to determine capture efficiency. Each of the tubes was exposed to one liter of 1 ppm PFIB gas in air followed by about 9 liters of ambient air (as flush for the source bulb). GC analysis of PFIB in the gaseous effluent from the tubes showed the two types of SKC silica tubes, untreated and treated with ammonium hydroxide, did not remove PFIB effectively (about 50 percent recovery) while untreated and treated charcoal tubes did remove PFIB effectively.

Each of the charcoal tubes were eluted with three 200 µL aliquots of concentrated ammonium hydroxide and then with 1 mL deionized water and finally with 5 mL of TISAB-B solution. Fluoride ion levels were determined with the ISE as described in Example 1. Recovery of PFIB as indicated by measurement of fluoride ion from treated charcoal tubes was 75 percent of the theoretical fluoride; tubes not pretreated gave PFIB recoveries of 50 percent as determined by the measurement of fluoride ion.

The results of this Example show that PFIB reacted efficiently with ammonium hydroxide when immobilized on a high surface area solid support.

Example 3

Quantitative Determination of PFIB

Four SKC charcoal sampling tubes were each pretreated with 200 µL ammonium hydroxide as described Example in 2. Each of the tubes was exposed to one liter of 1 ppm PFIB gas in air followed by approximately 9 liters of ambient air (as flush for the source bulb). The charcoal tubes were processed in steps: 1) the tubes were opened and separated—the front section of charcoal and the backup section poured into individual polystyrene (PS) culture tubes; 2) 200 µL of concentrated ammonium hydroxide were added to the charcoal in each PS tube and the poly cap was applied (total of eight tubes). The tubes were shaken and allowed to equilibrate for five minutes; 3) 2 mL of 4 molar TISAB-B was added to each tube, the cap was re-sealed, and the tubes were shaken; 4) Fluoride concentration was measured for each tube using the ISE as described in Example 1.

The advantage of gas sampling is that a large volume of gas may be swept through a small cartridge to effect concentration of the analyte of interest, PFIB in this case. In a second trial to further evaluate dynamic gas phase analysis, an apparatus was constructed to deliver a known concentration and flow rate of PFIB in a large volume of air or nitrogen. For each sample a microprocessor controlled syringe drive (from Hamilton Co., Reno, Nev.) with a polypropylene 50 cc syringe was used to deliver a constant flow of a relatively concentrated (between 300 and 10,000 µL PFIB per L air) PFIB-air mixture into a mixing tee. An air stream was delivered into the mixing tee via a line with an over-pressure by-pass, and the total flow through the tee past the PFIB delivery port was controlled by a calibrated Industrial Hygiene sampling pump (Industrial Hygiene Specialties, Columbus, Ohio). After passing through a short length of polyethylene tubing the dilute PFIB/nitrogen solution was directed through a pre-treated (as described in Example 2) ammonium hydroxide-on-charcoal sorbent tube. Sample tubes were processed as described in Example 2, and recovery of fluoride ion derived from PFIB was quantitative.

The data of Table 1 below show that the efficiency of large volume sampling approached 100 percent for quantitative determination of PFIB concentrations between 3.4 ppb and 100 ppb in a gas sample. At 10,000 ppb the capacity of this system was exceeded such that not all of the fluorine was recovered as fluoride.

TABLE 1

Large Volume Sampling* for Low Level PFIB by Sorption and Measurement of Fluoride

| Sweep Volume | PFIB concentration | Fluoride % Recovery | Replicate Precision |
|---|---|---|---|
| 10 liters | 10,000 ppb | 69% | +/− 1% |
| 10 liters | 10,000 ppb | 61% | +/− 0% |
| 10 liters | 100 ppb | 113% | +/− 6% |
| 10 liters | 100 ppb | 101% | +/− 6% |
| 50 liters | 55.1 ppb | 112% | +/− 3% |
| 50 liters | 8.0 ppb | 109% | +/− 5% |
| 50 liters | 3.4 ppb | 99% | +/− 5% |

*Sampled at a rate of 1 liter per minute for 10 liters and at a rate of 5 liters per minute for 50 liters Perfluoropropene (hexafluoropropene, HFP) was evaluated for its reactivity in the gas phase capture mode. It reacted with ammonium hydroxide, and was apparently less reactive than PFIB, since HFP was trapped at only 70 percent efficiency as determined by release of fluoride ion.

The quantitative defluorination of PFIB was developed into a simple field method for measurement of PFIB via measurement of the fluoride ion levels. This Example showed that defluorination of PFIB could be performed in a quantitative, exhaustive and reproducible manner to give a useful analytical method for the indirect measurement of PFIB at ppb concentrations in a fluid medium.

Example 4

Reactions of PFIB with Cyclic Amine Nucleophiles to Form Stable Adducts

Amine compounds were evaluated for their ability to form PFIB adducts. Morpholine-fluoroalkene adducts were preferred when stable adducts of fluoroalkene mixtures were desired for analytical or separation purposes. This Example showed that the addition of secondary amine nucleophiles to PFIB with the subsequent elimination of HF can form stable adducts. Production of the adducts were confirmed by the GC/MS method of Example. 5 below. Equation 1 illustrates the specific example of morpholine reacting with PFIB.

$$C_4H_8ONH+CF_2=C(CF_3)_2 \rightarrow C_4H_8ONCF=C(CF_3)_2+HF \qquad 1$$

The mass spectrum of the PFIB-morpholine adduct showed a base peak of m/z 223 and other significant peaks at m/z 267, m/z 248, m/z 209, m/z 208, and m/z 69. The expected molecular ion of the adduct at m/z 287 was not observed in the spectrum. It was postulated that the PFIB-morpholine adduct lost HF in solution prior to injection for GC/MS analysis. This hypothesis was supported by chemical ionization mass spectrometry analyses of the PFIB-morpholine standards using both methane and isobutane as the reagent gases. These analyses showed only two significant ion masses, one at m/z 268 which corresponded to the protonated molecular ion and one at m/z 248 which appeared to result from the loss of HF from the protonated molecular ion. Suggested fragmentation/rearrangement pathways are summarized in Reaction Sequence 2, below. The m/z 223 ion may represent a unique ion mass characteristic of PFIB adducts produced by reaction with cyclic secondary amines. This ion mass was also observed in the mass spectra of the adducts produced by reaction of PFIB with pyrrolidine and piperidine.

Reaction Sequence 2
Tentative M.S. Fragmentation/Rearrangement Pathways for PFIB-Morpholine Adduct

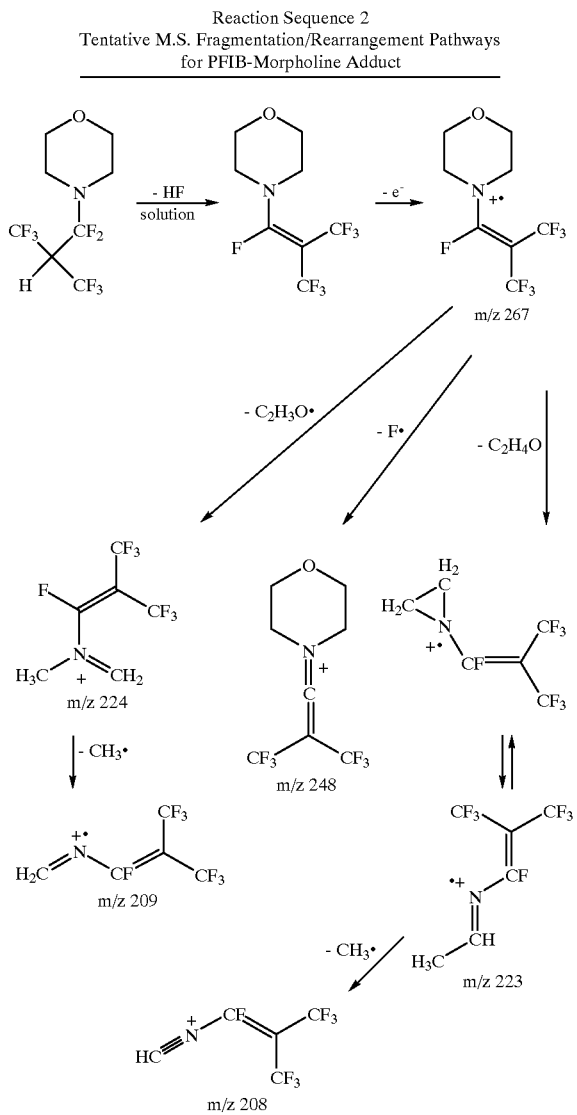

The m/z 248 ion resulted from the loss of F from the m/z 267, while the origin of the m/z 209 and m/z 208 ion mass were less obvious. The m/z 208 ion mass is believed to have resulted from the loss of $CH_3 \cdot$ from the m/z 223 ion and the m/z 209 ion mass from the loss of $CH_3 \cdot$ from the m/z 224 ion.

Example 5

Reaction of Fluoroalkenes with Nucleophile-coated Substrates

Various substrates were evaluated for their ability to remove fluoroalkenes. The substrates included high surface area activated silica gel (Aldrich Chemical Company, Milwaukee, Wis.) and Silicalite™ molecular sieves as well as these substrates coated with nucleophiles. The fluoroalkene removal efficiencies were determined for deactivated-silica gel, activated-silica gel, and with nucleophiles immobilized on silica gel. Evaluations were carried out by passing fluoroalkenes through 4 mm internal diameter glass tubes that were approximately 75 mm long and packed with coated or uncoated sorbents. The fluoroalkenes were passed through the tubes using 20 mL or 50 mL glass syringes. One syringe contained the fluoroalkene (1,000 ppm in air) used to challenge the silica gel, while the other was used to collect the gas that had passed through the tube. The fluoroalkene was passed through the silica gel tubes at approximately 1 mL per second. The fluoroalkenes that were evaluated included perfluoro-2-butene and 2H-pentafluoropropene.

Both perfluoro-2-butene and 2-hydro-pentafluoropropene were completely retained on activated silica gel. When the silica gel was deactivated by ambient moisture, or by the addition of 5% by weight water, neither fluoroalkene was retained. In addition, 2-hydro-pentafluoropropene was not desorbed from the activated silica gel using methyl-t-butyl ether (MTBE) elution solvent. However, when the MTBE elution solvent contained 5% by volume of morpholine, the 2-hydro-pentafluoropropene was quantitatively desorbed initially as the unreacted fluoroalkene. Subsequent re-analyses (next day) of the eluting solvent showed that the 2-hydro-pentafluoropropene had reacted with morpholine in the solution to form the 2-hydro-pentafluoropropene-morpholine adduct with subsequent spontaneous elimination of HF.

Both perfluoro-2-butene and 2-hydro-pentafluoropropene were retained on silica gel coated with approximately 10 weight percent morpholine based upon the weight of silica gel. Approximately 98% of the perfluoro-2-butene was retained, while 100% of the 2-hydro-pentafluoropropene was retained. When the silica gel was coated with piperazine, only 28% of the perfluoro-2-butene was retained. Similar trials using Silicalite coated with 5% morpholine or N-methylethylenediamine showed that 99-100% of the perfluoro-2-butene was retained. Silicalite™ was the preferred absorbent substrate since it was not de-activated by water.

Table 2 lists molecular ions and base peak ions observed in the MS analyses of a series of fluorinated alkene adducts with morpholine. This table also summarizes the relative reaction rates of fluoroalkenes with morpholine.

TABLE 2

Morpholine-Perfluoroolefin Adducts

| Fluorocarbon | Speed of Reaction* | Molecular Ion (m/z) | Base Peak (m/z) |
|---|---|---|---|
| 1-perfluoropropene | Fast | 237 | 136 |
| 2-hydropentafluoropropene | Fast | 199 | 199 |
| 2-perfluorobutene | Slow | 267 | 267 |
| Perfluorocyclobutene | Intermediate | 229 | 229 |
| 1-perfluoropentene | Fast | 317 | 317 |
| 1,3-hexafluorobutadiene | Fast | 229 | 229 |
| perfluoroisobutene | Fast | 267 | 223 |
| perfluoroethylene | Intermediate | 187 | 136 |
| perfluoro-3-methyl-1-butene | Fast | 337/317 | 136/248 |
| octafluorocyclopentene | Fast | 279 | 279 |
| 1,1-dihydrodifluoroethylene | No Rx | — | — |

*FAST means reaction is complete in 30 minutes or less
INTERMEDIATE means between 30 minutes and 3 hours
SLOW means greater than 3 hours 1,2-dihydrotetrafluoroethane and 1,2-dihydrohexafluoropropane did not react with morpholine in comparison to the fluoroalkene species, thus allowing the adduct formation to be useful in removing or quantifying fluororalkenes in bulk quantities of these fluoroalkane fluids.

Example 6

Specificity of N-methylaniline for PFIB Nucleophile—Adduct Formation

The amines listed in Table 3, below, were evaluated for reactivity with PFIB using the following procedure: The samples were prepared in glass autosampler vials having Teflon™ lined-rubber septum crimp caps (Kimble Glass, Vineland, N.J.). Portions of each of the amines were diluted with methyl t-butyl ether (MTBE) to produce 10% (v/v) solutions. Aziridine was purchased from Columbia Organic Chemicals, Columbia, S.C. A 1 mL volume of each amine solution was transferred to separate vials which were then capped. A 1 mL volume of a 10,000 ppm (v/v) standard of perfluoroisobutene (PFIB) in air was then introduced into the headspace of each vial using a gas-tight syringe. The vials were gently shaken for several minutes, then placed into the autosampler tray of the chromatograph for analysis. Analyses were obtained using GC/MS as described in Example 4. N-methylaniline was highly selective, forming an adduct with PFIB exclusively, under the test conditions described.

TABLE 3

Nucleophiles Reacted with PFIB

| Nucleophile | Product |
| --- | --- |
| Ammonia | Tricyanomethane + HF |
| Aziridine | Adduct − HF |
| Benzenethiol (Thiophenol) | " |
| Benzylamine | No Reaction under conditions employed |
| Dibenzylamine | " |
| Methylamine | Adduct − HF |
| Propylamine | " |
| Dimethylamine | " |
| Diethylamine | " |
| Dipropylamine | " |
| Dibutylamine | " |
| Dicyclohexylamine | " |
| Ethylenediamine | No Reaction under conditions employed |
| 2-Methoxyethylamine | " |
| Morpholine | Adduct − HF |
| N-Methylaniline | " |
| Methylbenzylamine | " |
| Piperidine | " |
| Pyrrole | " |
| pyrrolidine | " |
| Pyrrolidinone | Adduct |
| Piperazine | Adduct − 2HFs |

Example 7

Reactions of Fluoroalkene-nucleophile Adducts to Form Secondary Reaction Products The fluoroalkene-nucleophile adduct solutions of Example 6, comprising olefinic amine adducts resulting from the spontaneous elimination of HF, were treated with water or methanol to provide a 2 percent volume/volume solution. A secondary reaction involving addition of water or alcohol to the fluoroalkene-amine adduct was observed by the GCIMS analysis method described in Example 4.

The GC/MS data indicated that the initial water or methanol adducts also underwent further elimination reactions to form an amide (from water) and a vinyl ether (from methanol). The amide and vinyl ether thus formed were considered to be more stable than a) the initial adduct before the first HF elimination, b) the resultant olefinic amine adduct, and c) the water and alcohol addition product adducts. This series of reactions for the morpholine adduct of PFIB is illustrated in Reaction Sequence 3. The final amide (V) and vinyl ether (VII) were not as readily susceptible to further addition or hydrolysis reactions.

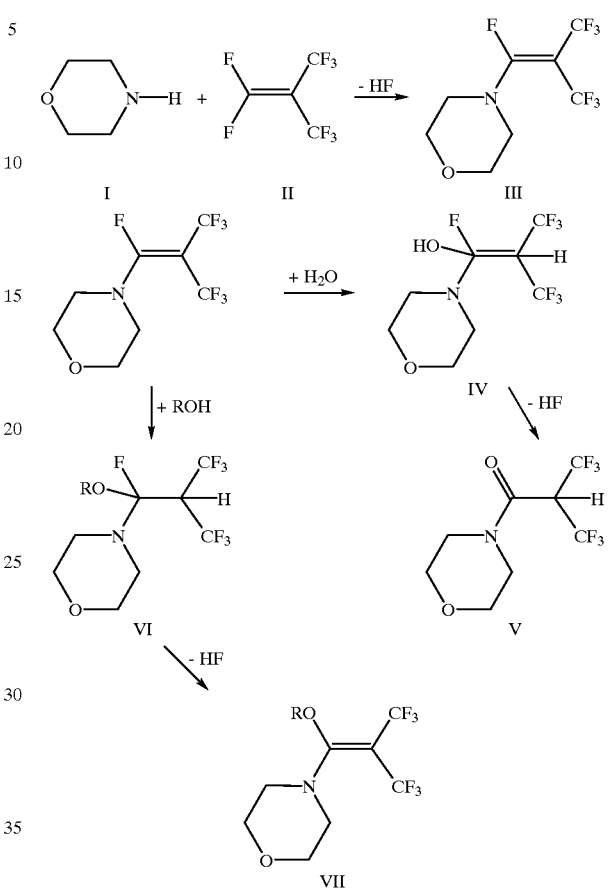

Reaction Sequence 3
Amide Formation by Hydrolysis of Morpholine-PFIB Adduct

Example 8

Identification and Quantification of Fluoroalkenes

Instrument calibration standards were prepared by passing a known volume of air spiked with a known volume of PFIB through a tube packed with morpholine-treated silica gel at a maximum rate of 0.5 L/min. The PFIB-morpholine adduct was then eluted from the tube with methyl tert-butyl ether (MTBE) and the resulting solution serially diluted to produce the standard calibration solutions. The lowest concentration standard was 13 parts-per-billion (ppb). The calibration curves prepared from both the fill scan and selective ion monitoring (SIM) analyses were linear over several orders of magnitude. In principle, the lower calibration limit may be extended from 13 ppb down to at least 100 parts-per-trillion (ppt) using SIM data acquisition. Generation of standards in this manner would compensate for incomplete reaction to form the adduct or incomplete recovery of the adduct from the silica gel, assuming an unknown sample was treated similarly to the standards.

Standard solutions and sample extracts were analyzed using combined capillary column gas chromatography/low resolution mass spectrometry (GC/MS). The initial analyses were carried out using full scan mass spectrometry. The later analyses were carried out using (SIM) mass spectrometry which provided better sensitivity. Standard solutions and sample extracts were analyzed using a Hewlett Packard Model 5970 Mass Selective Detector (MSD) interfaced to a Hewlett Packard Model 5890 Gas Chromatograph (Hewlett Packard Co., Instruments Division, Palo Alto, Calif.). The mass spectrometer was scanned between 35-350 amu for the full scan analyses and selectively jumped between m/z 223 and m/z 267 for the SIM analyses. Electron impact ionization (EI) at a nominal 70 eV was used. Components in the MTBE solutions were separated using a 30 meter DB-5 capillary column having an internal diameter of 0.25 mm and a film thickness of 1 um. The gas chromatograph was operated with a constant column head pressure of 69 kPa and a temperature program of 10° C./minute from 40° C. to 300° C. The column temperature was held at the initial temperature for one minute before programming and the injector temperature was maintained at 250° C. Using these conditions, the PFIB-morpholine adduct was completely separated from the solvent, the excess morpholine, and from other compounds present in the extracts. Of the two ion masses monitored for the SIM analyses, the m/z 223 ion was the most unique and exhibited the least response to other compounds present in the extract.

Example 9

Reaction of PFIB with a Sulfur Containing Nucleophile

Thiophenol was reacted with PFIB using the procedure described in Example 6. A stable adduct was formed which could be isolated and identified by GC/MS. Molecular ions with m/z of 310 and 290 were detected which indicated that both the original thiophenol-PFIB adduct and the adduct after elimination of HF were present. Reaction Sequence 4 below, illustrates the reaction and proposed mass spectrometric ion mass assignment fragmentation patterns observed.

Reaction Sequence 4
Reaction of Thiophenol with PFIB

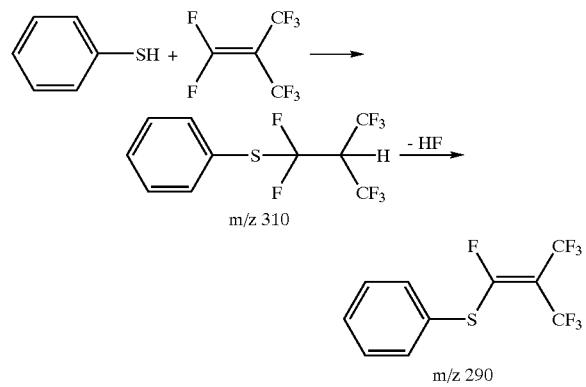

Example 10

Reaction of PFIB with a Phosphorous Nucleophile

Trimethylphosphite (TMP) reagent was prepared by adding 22.5 microliters of TMP to 1.5 mL of acetonitrile in a sealed autosampler vial. A polypropylene syringe was used to add 1.0 mL of this reagent to each of the vials containing 15 mL of a) standards of PFIB in perfluorohexane and b) test samples. The sample vial was placed on a shaker at high speed for three hours, the acetonitrile layer was transferred to an autosampler vial, and the sample was immediately analyzed by GC. Chromatographic conditions were: HP5890 gas chromatograph with Electron Capture detector and HP7673A autosampler (Hewlett Packard, Palo Alto, Calif.); 30 meter DB-210 column with 0.32 mm internal diameter and 0.5 μm film thickness; Nitrogen carrier/makeup gas; Oven program 60° C. initial to 160° C. final programmed at 5 deg. per minute for a 20 minute run; Injection port 120° C.; Detector temperature 240° C.; Splitless injection with 1 microliter sample size.

Reaction Sequence 5 illustrates the proposed reaction products. Structure VIII was the major adduct, confirmed by mass spectrometry. It is believed that trimethyl phosphite is specific for PFIB and does not form adducts with other less reactive fluoroalkenes.

Three product peaks were generated in the chromatograms, consistent with three products from this reaction. The first product (VII) was converted to the other two. The earliest eluting chromatographic peak was used for calibration and quantitation. Detection limit was established as ten parts per billion (ppb). Table 4 gives recovery data for this method.

Reaction Sequence 4
Reaction of Thimethylphosphite with PFIB

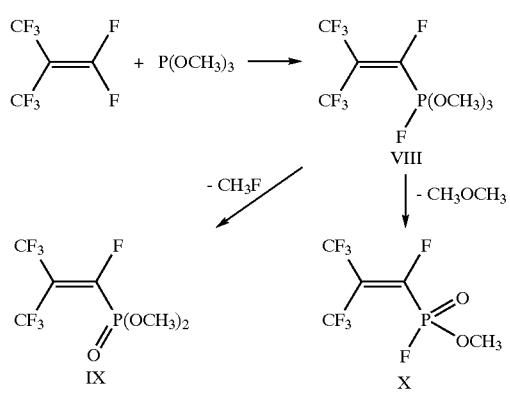

TABLE 4

Recovery of PFIB by Different GC Methods and in Different Fluids

| | | PFIB Found (ppb) | |
|---|---|---|---|
| Fluid | PFIB Expected (ppb) | Direct GC Carbopack B | TMP Derivatization DB 210 |
| Perfluorooctane | 50 | 43 ± 6.2 (n = 5) | 52 ± 3.6 (n = 5) |
| Perfluoro-hexane | 20 | analysis not possible | 18 ± 3.2 (n = 5) |

Example 11

PFIB-morpholine Adduct Formation Using Particle Loaded Membranes

Porous particle loaded membrane disks of four types were tested for their ability to remove PFIB from a gaseous stream and to form the PFIB-morpholine adduct in-situ. The membranes used were 3M PTFE matrix Empore™ membranes containing 1) octadecylsilane bonded silica, 2) styrene-divinylbenzene resin, 3) carbon, (all available from Fisher Scientific, Pittsburgh, Pa.) and 4) Silicalite™ enmeshed in a polypropylene matrix (from 3M Co. St. Paul, Minn. as described in U.S. Pat. No. 5,529,686, Example 3). The disks were approximately 0.5 mm thick and 25 mm in diameter. They were held in a stainless steel filter holder (Millipore Corp., Bedford, Mass.). They were tested for their ability to sorb PFIB as 1) received (or un-treated) and 2) treated with morpholine. The treated disks were prepared by soaking the disks in a 10 volume % solution of morpholine in methyl tert-butyl ether solvent. They were removed from the solution and allowed to air dry for 24 hours to remove the volatiles.

One hundred mL gas sampling bulbs containing 1000 ppm by vol PFIB in air were prepared as described in Example 1. The 100 mL bulb was connected to membrane holder in series with a 1.27 cm long 26 gauge hypodermic needle acting as a flow restrictor. The flow restrictor was connected to an evacuated 1000 mL gas sampling bulb which was used to draw the contents of the 100 mL sample bulb through the membrane being tested. The flow rate was measured and found to be 0.2 liters per minute.

PFIB levels in the 1000 mL bulb acting as a receiver for the contents of 100 mL sample bulb were analyzed by GC as described in Example 2. Of the untreated membrane disks tested, only the carbon disk membrane was effective in removing the PFIB, as evidenced by the absence of PFIB in the receiver bulb. The other untreated disks were not effective in retaining PFIB by sorption. When coated with morpholine, all of the disks were effective at removing PFIB by sorption or reaction, as evidenced by the absence of PFIB in the receiver bulbs.

A Silicalite loaded membrane disk (treated with morpholine and exposed to PFIB as described above) was removed from its holder and extracted with MTBE to establish the proposed PFIB morpholine adduct formation under these conditions. The extract was analyzed by GC/MS as described in Example 8 and was found to contain the adduct showing that the reaction with PFIB was rapid under these conditions. Small amounts of hexafluoropropylene, perfluoro-1-butene, and perfluoro-2-butene were present in the PFIB gas standard and these were not retained by, nor did they form adducts with, the morpholine coated disks under the conditions of this example. The rates of reaction of PFIB with nucleophiles are known to be faster than with other fluoroalkenes and these conditions were insufficient for the fluoroalkenes with slower reaction rates. Slower flow rates, thicker disks (longer pathlengths), and larger diameter disks can be used to increase the residence times of those analytes in the disk to allow for optimum reaction conditions.

This example showed that nucleophile-coated, high surface area particles, entrapped in porous fibril matrices can effectively serve as reaction media for removing PFIB from fluids.

The data of the examples of the present invention clearly show that the formation of fluoroolefin-N, -S, or -P nucleophile adducts provided a means of converting, removing, identifying, and quantifying fluoroolefins such as PFIB in fluids. The ability to form unstable adducts as with ammonium hydroxide provided a method for destruction of toxic fluoroolefins, such as PFIB, for remedial purposes. The formation of stable adducts provided a means for immobilizing and for positively identifying and quantifying fluoroolefins in fluids such as gas and liquids. The use of organic nucleophiles to convert volatile and/or toxic fluoroolefins to a relatively less toxic and lower volatility species is of great utility. Fluoroolefin products, obtained by HF eliminations from primary fluoroalkene-nucleophile adducts, were themselves capable of further reactions with nucleophiles such as water and alcohols to form stable and useful products such as fluorinated amides and vinyl ethers when N-nucleophiles were used.

Various modifications and alterations of this invention will become apparent to those skilled in the art without departing from the scope and intent of this invention, and it should be understood that this invention is not to be unduly limited to the illustrative embodiment set forth herein.

We claim:

1. A method for removing perfluoroisobutene from a fluid comprising the step of contacting the fluid with N-methylaniline for a time sufficient to form an N-methylaniline-perfluoroisobutene adduct.

2. The method according to claim 1 wherein said N-methylaniline-perfluoroisobutene adduct is bonded or sorbed to a support.

3. The method according to claim 2 wherein said support is selected from the group consisting of (a) organic polymeric supports which optionally can be clad with a sorptive coating; (b) inorganic particulate supports which optionally can be clad with a sorptive coating; and (c) carbon particulates.

4. The method according to claim 2 wherein said support is a particulate support.

5. The method according to claim 4 wherein said particulate support is a molecular sieve.

6. The method according to claim 4 wherein said particulate support is enmeshed in a porous, fibrous web.

7. The method according to claim 6 wherein said porous, fibrous web is selected from the group consisting of fibrillated polytetrafluoroethylene, microfibrous webs, macrofibrous webs, and polymer pulps.

8. The method according to claim 4 wherein said particulate support is in a bed, column, or tube.

9. A method for quantifying perfluoroisobutene in a fluid comprising the steps of:
   a) providing an N-methylaniline-perfluoroisobutene adduct, said adduct being sorbed or bonded to a support, and
   b) displacing said adduct from said support for indirect quantification of perfluoroisobutene.

10. A method for quantifying perfluoroisobutene in a fluid comprising the steps of:
   a) providing an N-methylaniline-perfluoroisobutene adduct, said adduct being sorbed or bonded to a support, and
   b) measuring fluoride ion for indirect quantification of perfluoroisobutene.

11. A method for isolating perfluoroisobutene from a fluid comprising two or more fluoroalkenes comprising the step of contacting the fluid with N-methylaniline for a time sufficient to form an N-methylaniline-perfluoroisobutene adduct.

* * * * *

UNITED STATES PATENT AND TRADEMARK OFFICE
CERTIFICATE OF CORRECTION

PATENT NO.    : 6,437,202 B2
DATED         : August 20, 2002
INVENTOR(S)   : Mueller, Mark E.

It is certified that error appears in the above-identified patent and that said Letters Patent is hereby corrected as shown below:

<u>Title page,</u>
Item [62], Related U.S. Application Data, "Sep. 16, 1988" should read
-- Sep. 16, 1998 --

<u>Column 13,</u>
Line 47, "(FC $_{72}$." should read -- (FC 72, --

<u>Column 14,</u>
Line 21, "all the S fluorine" should read -- all the fluorine --

<u>Column 16,</u>
Line 45, "Example. 5" should read -- Example 5 --

<u>Column 17,</u>
Lines 50 and 51, "loss of $CH_3$." should read -- loss of $CH_3$ • --

Signed and Sealed this

Twenty-ninth Day of June, 2004

JON W. DUDAS
*Acting Director of the United States Patent and Trademark Office*